US012797241B2

(12) United States Patent
Labbe

(10) Patent No.: US 12,797,241 B2
(45) Date of Patent: Nov. 17, 2026

(54) OPHTHALMIC SURGICAL INSTRUMENT FOR CATARACT REMOVAL AND METHODS OF USE

(71) Applicant: Thad Anthony Labbe, Georgetown, TX (US)

(72) Inventor: Thad Anthony Labbe, Georgetown, TX (US)

( * ) Notice: Subject to any disclaimer, the term of this patent is extended or adjusted under 35 U.S.C. 154(b) by 0 days.

(21) Appl. No.: 18/581,117

(22) Filed: Feb. 19, 2024

(65) Prior Publication Data

US 2024/0189144 A1 Jun. 13, 2024

Related U.S. Application Data

(63) Continuation-in-part of application No. 18/074,981, filed on Dec. 5, 2022, now abandoned, which is a continuation of application No. 17/083,268, filed on Oct. 28, 2020, now Pat. No. 11,517,475, which is a continuation of application No. 16/701,080, filed on Dec. 2, 2019, now abandoned, which is a continuation-in-part of application No. 16/112,693, filed on Aug. 25, 2018, now abandoned.

(51) Int. Cl.

| | |
|---|---|
| ***A61F 9/007*** | (2006.01) |
| ***A61B 17/285*** | (2006.01) |
| *A61B 17/00* | (2006.01) |
| *A61B 17/28* | (2006.01) |

(52) U.S. Cl.
CPC .................... *A61F 9/00754* (2013.01); *A61B 2017/00398* (2013.01); *A61B 17/282* (2013.01); *A61B 17/2841* (2013.01); *A61B 2017/2845* (2013.01); *A61B 17/285* (2013.01)

(58) Field of Classification Search
CPC ............. A61F 9/00754; A61F 9/00781; A61F 9/00736; A61F 9/00745; A61B 17/282; A61B 17/2841; A61B 17/285; A61B 2017/00398; A61B 2017/2845
See application file for complete search history.

(56) References Cited

U.S. PATENT DOCUMENTS

| | | | |
|---|---|---|---|
| 3,683,891 | A | 8/1972 | Eskridge |
| 3,976,077 | A | 8/1976 | Kerfoot, Jr. |
| 4,000,745 | A | 1/1977 | Goldberg |
| 4,653,496 | A | 3/1987 | Bundy |
| 4,745,919 | A | 5/1988 | Bundy |

(Continued)

*Primary Examiner* — Jing Rui Ou
(74) *Attorney, Agent, or Firm* — HULSEY P.C.

(57) ABSTRACT

An ophthalmic surgical instrument for cataract removal and methods of use are disclosed. The ophthalmic surgical instrument includes a housing, a wire connecting the housing, and a helical corkscrew extending from the wire. The helical corkscrew has one or two 360 degrees turn configurations. The helical corkscrew has an interior passage and a beveled tip. The tip impales a cataract by creating an opening in the cataract. The helical corkscrew is twisted such that the tip rotates inside of the cataract allowing removal of the fluid at different depths, and pushes up pieces of the cataract for removal. The housing connects to an ultrasound handpiece for transmitting ultrasound waves to break up the cataract and suck out the pieces of the cataract. The housing connects to a syringe body for injecting a viscoelastic into the eye through said helical corkscrew to keep the eye from collapsing during the use.

8 Claims, 3 Drawing Sheets

(56) References Cited

U.S. PATENT DOCUMENTS

| | | | |
|---|---|---|---|
| 4,935,025 | A | 6/1990 | Bundy |
| 5,135,530 | A | 8/1992 | Lehmer |
| 5,156,607 | A | 10/1992 | Kansas |
| 5,364,405 | A | 11/1994 | Zaleski |
| 5,437,678 | A | 8/1995 | Sorensen |
| 5,451,230 | A | 9/1995 | Steinert |
| 6,719,805 | B1 | 4/2004 | Ahern |
| 6,911,019 | B2 | 6/2005 | Mulier |
| 9,220,892 | B2 | 12/2015 | Faure |
| 9,993,231 | B2 | 6/2018 | Costello |
| 10,667,855 | B1 | 6/2020 | To |
| 2001/0031951 | A1 | 10/2001 | Pezzola |
| 2002/0026176 | A1 | 2/2002 | Varner |
| 2002/0091351 | A1 | 7/2002 | Rockley |
| 2002/0095113 | A1 | 7/2002 | Kishimoto |
| 2002/0111608 | A1 | 8/2002 | Baerveldt |
| 2002/0165522 | A1 | 11/2002 | Holmen |
| 2003/0004455 | A1 | 1/2003 | Kadziauskas |
| 2003/0050629 | A1 | 3/2003 | Kadziauskas |
| 2003/0055442 | A1 | 3/2003 | Laufer |
| 2003/0135226 | A1 | 7/2003 | Bolduc |
| 2003/0158567 | A1 | 8/2003 | Ben-Nun |
| 2004/0254520 | A1 | 12/2004 | Porteous |
| 2004/0254572 | A1* | 12/2004 | McIntyre ........... A61B 18/1477 606/41 |
| 2006/0020326 | A9 | 1/2006 | Bolduc |
| 2008/0140203 | A1 | 6/2008 | Davis |
| 2010/0152626 | A1 | 6/2010 | Schwartz |
| 2010/0189765 | A1* | 7/2010 | Erickson ................. A61P 27/02 424/427 |
| 2011/0077672 | A1* | 3/2011 | Fleischman ........ A61B 17/0401 606/232 |
| 2011/0264130 | A1 | 10/2011 | Glazer |
| 2012/0022434 | A1 | 1/2012 | Lue |
| 2012/0143226 | A1* | 6/2012 | Belson ............... A61B 17/0057 606/139 |
| 2015/0320597 | A1 | 11/2015 | Jacobovitz |
| 2017/0007452 | A1 | 1/2017 | Depenbusch |
| 2022/0160543 | A1 | 5/2022 | Gliner et al. |

* cited by examiner

OPHTHALMIC SURGICAL INSTRUMENT FOR CATARACT REMOVAL AND METHODS OF USE

The present application is a continuation-in-part of U.S. Non-Provisional application Ser. No. 18/074,981, filed Dec. 5, 2022; which is a continuation of U.S. Non-Provisional application Ser. No. 17/083,268, filed Oct. 28, 2020 (now U.S. Pat. No. 11,517,475); which is a continuation of U.S. Non-Provisional application Ser. No. 16/701,080, filed Dec. 2, 2019 (now abandoned); which is a continuation-in-part of U.S. Non-Provisional application Ser. No. 16/112,693, filed Aug. 25, 2018 (now abandoned); all of which are incorporated herein in their entirety and referenced thereto.

FIELD OF THE INVENTION

The present invention relates to surgical instruments for surgery of the eye. More specifically, the invention relates to an ophthalmic surgical instrument for removing a cataract during a cataract removal surgery.

BACKGROUND OF THE INVENTION

It is known that a cataract is an opacification or cloudiness of the eye's crystalline lens due to aging, disease, or trauma that typically prevents light from forming a clear image on the retina. Cataract increases the opacity of the lenses of the eyes. The result is gradual and progressive impairment of vision. Owing to the high prevalence of cataracts, cataract extraction is the most common eye surgery. Cataract surgeries vary in types, depending on the patient's condition and preferences.

Cataract surgery requires a standard set of cataract surgical instruments due to the delicate nature of the eyes. General instruments may be too large and coarse for use in this surgical procedure, which may do more damage than good. An example of a cataract surgical instrument is disclosed in a U.S. Pat. No. 5,364,405, entitled "Ophthalmic instrument with curved suction conduit and internal ultrasound needle" ("the '405 Patent"). The '405 Patent discloses an ophthalmic instrument including an elongated tube having proximal and distal end portions, a distal end and an elongated passage opening at a distal opening at the distal end. The distal end portion is sized to be received through an incision into the eye. An elongated member having a resiliently deformable end portion is at least partially received in the elongated passage of the tube. The distal end portion of the inner member has a curved configuration in a relaxed condition and is capable of performing a function within the eye. The tube and the inner member are relatively movable longitudinally so that the distal end portion of the inner member can be caused to project through the distal opening a variable amount to change the length of the arc of the curved configuration projecting from the distal opening. A hollow ultrasound needle is positioned in the inner member which is movable relative to the needle.

Another cataract surgical instrument is disclosed in a United States Publication No. 20220160543, entitled "Removal of cataract debris" ("the '543 Publication"). The '543 Publication discloses a phacoemulsification apparatus that includes actuators configured to vibrate responsively to respective driving signals, a needle including an aspiration channel, and configured to be vibrated by the actuators so as to emulsify a lens of an eye, a generator configured to generate at least one of the driving signals responsively to a vibration pattern selected for the needle, the needle being configured to vibrate in accordance with the selected vibration pattern, and a sensor configured to sense a level of vacuum in the aspiration channel, wherein the generator is configured to alter at least one of the driving signals to transition vibration of the needle from a first vibration pattern selected from the group consisting of a longitudinal vibration pattern and a first helical vibration pattern, to a second vibration pattern of a second helical vibration pattern, responsively to a decrease in the sensed level of vacuum.

In certain cases, an ultrasonic instrument is used to break up a cataract into small pieces and remove the cataract using vacuum. Sometimes, when using the ultrasonic instrument to remove a cataract, the piece of cataract may be resistant to being removed. A single helical corkscrew-like device attached to the end of the ultrasonic instrument can be helpful in grasping the whole cataract or a piece of the cataract.

When the cataract becomes whitened and the vision of the patient with the cataract becomes extremely blurry the cataract is known as a mature cataract. If the mature cataract develops an increase in pressure within its capsule, it is considered an intumescent cataract. The increased pressure inside the capsule can cause problems when the capsule is opened up at the time of cataract surgery. High intracapsular pressure can cause the capsule to tear rapidly and uncontrollably when the surgeon tries to open the capsule. This tearing out of the capsule is known as the Argentinian flag sign. This tearing of the capsule can lead to the loss of the cataract into the vitreous cavity. None of the above discussed cataract surgical instruments can be used for impaling the swollen cataract in a controlled manner.

Therefore, there is a need in the art to provide an ophthalmic surgical instrument having a corkscrew structure that can impale the swollen cataract in a controlled manner while reducing pressure inside the cataract.

SUMMARY OF THE INVENTION

It is an object of the present invention to provide an ophthalmic surgical instrument that avoids the drawbacks of known cataract surgical instruments.

It is another object of the present invention to provide an ophthalmic surgical instrument having a corkscrew structure that can impale the swollen cataract in a controlled manner.

It is another object of the present invention to provide an ophthalmic surgical instrument that can be used to reduce pressure inside a cataract.

In order to overcome one or more objects, the present invention presents an ophthalmic surgical instrument or a cataract surgical instrument. The ophthalmic surgical instrument includes a housing, a wire connecting the housing, and a helical corkscrew extending from the wire. The helical corkscrew has one or two 360 degrees turn configurations. The helical corkscrew has an interior passage and a beveled tip. The tip impales a cataract by creating an opening in the cataract. The helical corkscrew is twisted such that the tip rotates inside of the cataract allowing removal of the fluid at different depths, and pushes up pieces of the cataract for removal.

The housing connects to an ultrasound handpiece for transmitting ultrasound waves to break up the cataract and suck out the pieces of the cataract. Further, the housing includes a cutting member having a cutting interior. The cutting member vibrates and sucks the fluid through the cutting interior. In some embodiments, the housing connects to a syringe body for injecting a viscoelastic substance into the eye through the helical corkscrew to keep the eye from collapsing during the use.

In one advantageous feature of the present invention, the sharp bevelled tip/edge of the helical corkscrew is used to impale the piece of cataract or the whole cataract by creating a small opening in the cataract. Subsequently, the helical corkscrew is twisted such that the tip rotates inside of the substance of the lens/cataract and allows the eye surgeon to remove the fluid from the cataract at different depths. The 360-degree helical corkscrew helps to push up the broken pieces of the cataract and allows the eye surgeon to remove the cataract from the eye easily thereby avoiding Argentinian flag sign. This way, the ophthalmic surgical instrument offers the eye surgeon to impale the swollen cataract in a controlled manner.

In another advantageous feature of the present invention, the ophthalmic surgical instrument connect to a syringe having a viscoelastic substance. The viscoelastic substance is injected into the eye through the helical corkscrew to keep the eye from collapsing as ophthalmic surgical instrument is being used. Further, the viscoelastic substance allows the eye surgeon to go deeper into the eye to impale the swollen cataract in a controlled manner.

The features and advantages of the invention here will become more apparent in light of the following detailed description of selected embodiments, as illustrated in the accompanying FIGURES. As will be realized, the invention disclosed is capable of modifications in various respects, all without departing from the scope of the invention. Accordingly, the drawings and the description are to be regarded as illustrative in nature.

BRIEF DESCRIPTION OF THE DRAWINGS

A more complete understanding of the invention and its many advantages thereof will be readily appreciated as the same becomes better understood by reference to the following detailed description, when considered in connection with the accompanying drawings wherein.

DETAILED DESCRIPTION OF THE INVENTION

The following detailed description set forth below in connection with the appended drawings is intended as a description of exemplary embodiments in which the presently disclosed invention may be practiced. The term "exemplary" used throughout this description means "serving as an example, instance, or illustration," and should not necessarily be construed as preferred or advantageous over other embodiments. The detailed description includes specific details for providing a thorough understanding of the presently disclosed ophthalmic surgical instrument. However, it will be apparent to those skilled in the art that the presently disclosed invention may be practiced without these specific details. In some instances, well-known structures and devices are shown in functional or conceptual diagram form in order to avoid obscuring the concepts of the presently disclosed ophthalmic surgical instrument.

In the present specification, an embodiment showing a singular component should not be considered limiting. Rather, the invention preferably encompasses other embodiments including a plurality of the same component, and vice-versa, unless explicitly stated otherwise herein. Moreover, the applicant does not intend for any term in the specification to be ascribed an uncommon or special meaning unless explicitly set forth as such. Further, the present invention encompasses present and future known equivalents to the known components referred to herein by way of illustration.

Although the present invention provides a description of an ophthalmic surgical instrument, it is to be further understood that numerous changes may arise in the details of the embodiments of the ophthalmic surgical instrument. It is contemplated that all such changes and additional embodiments are within the spirit and true scope of this disclosure.

The following detailed description is merely exemplary in nature and is not intended to limit the described embodiments or the application and uses of the described embodiments. All of the implementations described below are exemplary implementations provided to enable persons skilled in the art to make or use the embodiments of the disclosure and are not intended to limit the scope of the disclosure.

Various features and embodiments of an ophthalmic surgical instrument for cataract removal are explained in conjunction with the description of FIGS. (FIGS.) 1-3.

Figure 1:
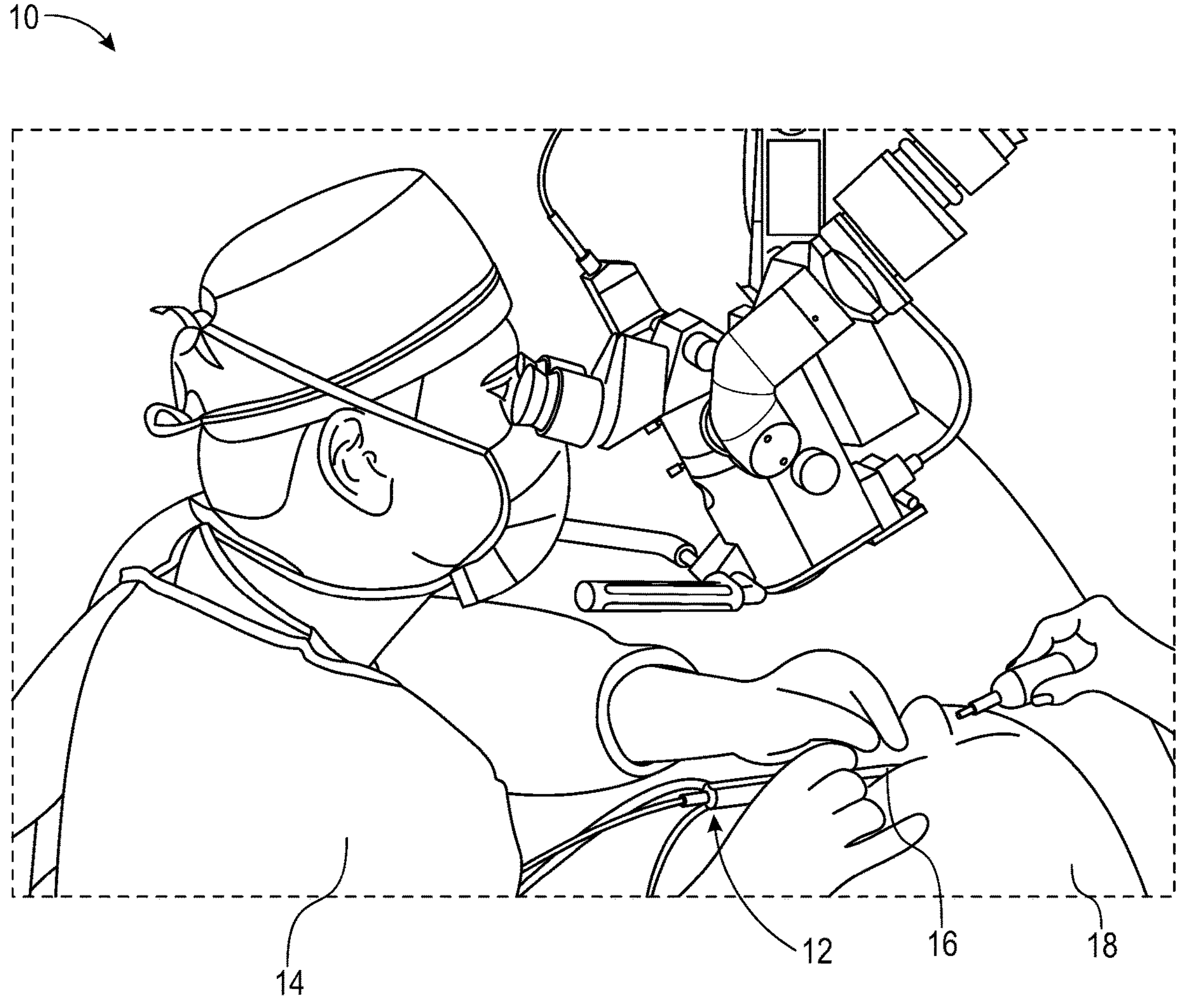
FIG. 1 illustrates an environment in which an ophthalmic surgical instrument implements, in accordance with one embodiment of the present invention.

FIG. 1 shows an environment 10 in which an ophthalmic surgical instrument 12 implements, in accordance with one embodiment of the present invention. Ophthalmic surgical instrument 12 indicates a medical device or surgical device or cataract removal device or cataract surgical instrument used by an eye surgeon 14 during a cataract removal surgery of an eye 16 of a patient 18.

Figure 2:
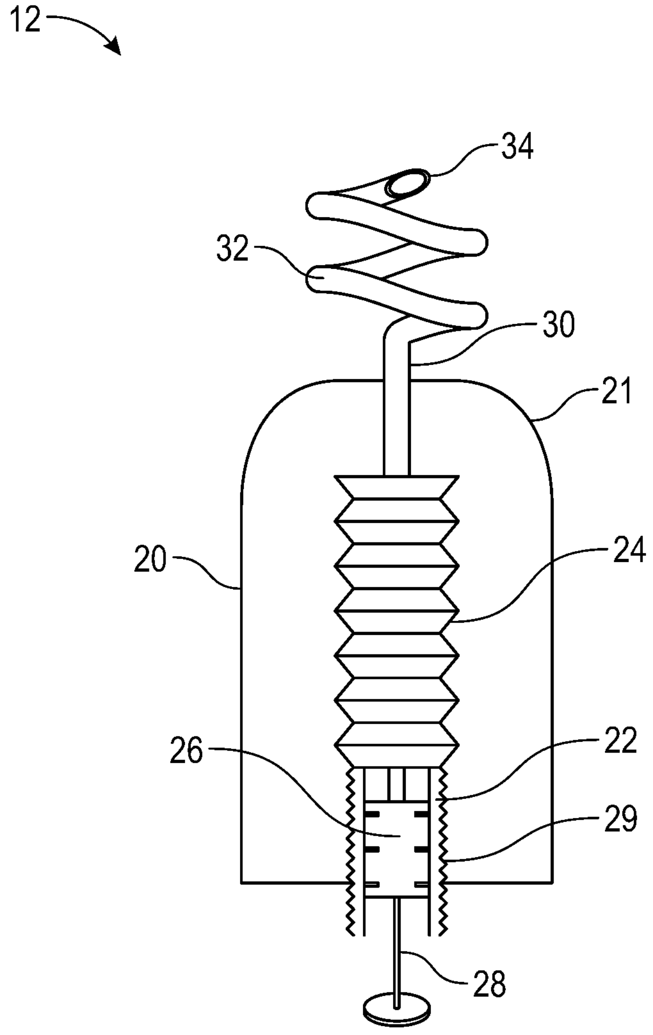
FIG. 2 illustrates the ophthalmic surgical instrument, in accordance with one embodiment of the present invention.

FIG. 2 shows a schematic view of ophthalmic surgical instrument 12, in accordance with one embodiment of the present invention. Ophthalmic surgical instrument 12 includes a housing 20. Housing 20 has a cylindrical configuration with curved edges 21. Curved edges 21 allow ophthalmic surgical instrument 12 to pass into the eye while catching endothelium (not shown). Housing 20 includes a syringe body 22 having a corrugated section 24. Corrugated section 24 extends from syringe body 22. Syringe body 22 presents an interior 26. Further, syringe body 22 includes a plunger 28 at the bottom. Syringe body 22 fits into housing 20 such that plunger 28 is operated to provide negative pressure to decrease intralenticular pressure once lens or cataract is impaled. In one example, syringe body 22 includes a threaded portion 29. Threaded portion 29 helps to hold housing 20 and turn or syringe body 22 so as to move syringe body 22 or helical corkscrew 30 forward.

Further, syringe body 22 encompasses a helical corkscrew 30. In the present invention, helical corkscrew or helical tube 30 has a two 360 degree turns configuration. Helical corkscrew 30 has an interior passage 32. Here, interior passage 32 indicates a channel in helical corkscrew 30. Further, helical corkscrew 30 has a sharp tip 34. In one example, tip 34 has a sharp bevelled edge/tip. In another example, tip 34 is angled depending on the need. Tip 34 helps to impale the lenses during the cataract removal surgery.

Ophthalmic surgical instrument 12 is used to impale the swollen cataract in a controlled manner. In order to operate ophthalmic surgical instrument 12, at first, interior 26 of syringe 22 is filled with a viscoelastic substance. In use, the viscoelastic substance is injected into the eye to form the eye and to keep the eye from collapsing as ophthalmic surgical instrument 12 is being used. Further, helical corkscrew 30 is screwed into the cataract by advancing ophthalmic surgical instrument 12. Further, helical corkscrew 30 is slowly turned/twisted in order to impale and grasp a cataract piece. As helical corkscrew 30 is turned, tip 34 pushes up the broken pieces of the cataract for easy removal. This ensures the cataract does not fall into the vitreous cavity. Helical corkscrew 30 is removed from the eye to remove different pieces of cataract from the eye. In addition, a grasping device (not shown) may be used to grasp the whole lens by being twisted into the substance of the cataract. Additionally, a cutting instrument such as a horizontal chopper might be used to break up the cataract. Whenever needed, plunger 28 is operated to provide negative pressure to decrease intralenticular pressure once lens is impaled.

Figure 3:
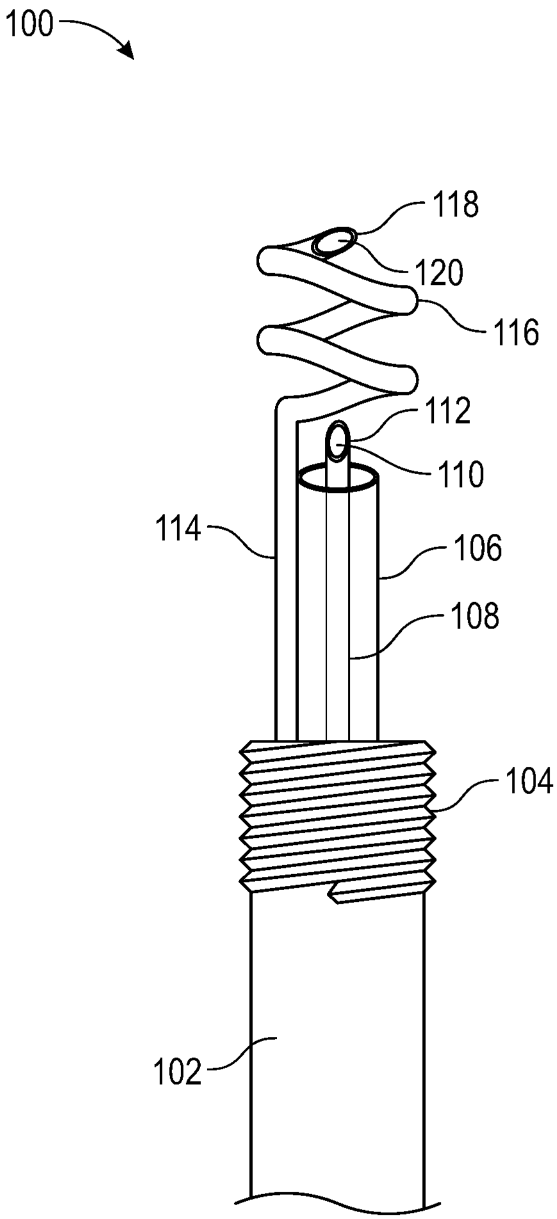
FIG. 3 illustrates an ophthalmic surgical instrument having a syringe holding a viscoelastic substance, in accordance with one embodiment of the present invention.

FIG. 3 shows a schematic view of ophthalmic surgical instrument 100, in accordance with another embodiment of the present invention. Ophthalmic surgical instrument 100 includes an ultrasound handpiece or ultrasonic instrument 102. Ultrasound handpiece 102 indicates a phacoemulsification probe or ultrasonic probe used to trench, emulsify, and aspirate the cataractous lens. Ultrasound handpiece 102 connects to a cylindrical housing 106 via a threaded portion 104. Cylindrical housing 106 encompasses a cutting member 108 having an interior or cutting interior 110. Cutting member 108 has a first tip 112 having a bevelled edge.

Further, ophthalmic surgical instrument 100 includes a wire 114. Wire 114 extends parallel to cylindrical housing 106. In the present embodiment, wire 114 is positioned adjacent to cylindrical housing 106 allowing ophthalmic surgical instrument 100 to be inserted into the front of the eye. Wire 114 includes a helical corkscrew 116. In the present invention, helical corkscrew or helical tube 116 has one or two 360 degrees turn configurations depending on the need. Here, helical corkscrew 116 having a single 360 degrees turn configuration is presented. Helical corkscrew 116 has an interior passage 118. Here, interior passage 118 indicates a channel in helical corkscrew 116. Further, helical corkscrew 116 has a sharp tip 120. In one example, tip 120 has a sharp bevelled edge. In another example, tip 120 is angled depending on the need.

In order to operate ophthalmic surgical instrument 100, housing 106 is attached to ultrasound handpiece 102. Further, eye surgeon 14 engages ultrasonic handpiece 102 to transmit ultrasound waves to break up (emulsify) the cataract. Further, tip 120 of helical corkscrew 116 is used to impale the piece of cataract or the whole cataract. Specifically, the sharp tip 120 is rotated into the cataract to provide grasping power. A person skilled in the art understands that helical corkscrew 116 is twisted by hand to impale a piece of the cataract or helical corkscrew 116 is twisted the other way to bring the impaled piece of cataract closer to the ultrasonic handpiece 102 to allow phacoemulsification to occur.

Helical corkscrew 116 is screwed into the cataract so that fluid can be sucked out of the cataract from different depths of the swollen lens. Fluid from inside of the cataract is removed from different depths inside of the cataract to help lower the intracapsular pressure. Once screwed inside the substance of the cataract, the 360 degrees turn of helical corkscrew 116 is used to press against the cataract to help ease any fluid inside the capsule to come out of the cataract. Subsequently, helical corkscrew 116 is twisted out of the capsular bag so that the capsule remains with only one small hole. Once the intracapsular pressure has been controlled with ophthalmic surgical instrument 100, a controlled capsulorhexis is made safely.

As specified above, eye surgeon 14 engages ultrasonic handpiece 102 to transmit ultrasound waves to break up (emulsify) the cataract and suck out broken fragments of the cataract. Here, operating ultrasonic handpiece 102 causes cutting member 108 positioned in a vertical/straight configuration to vibrate and suck the fluid through interior 110. Further, cutting member 108 helps to inject the fluid around the outer part of cutting member 108 to protect the cornea when cutting member 108 is going into the eye.

It should be understood that ophthalmic surgical instrument 100 having helical corkscrew 116 can be used with syringe 22 as explained above to inject the viscoelastic substance without departing from the scope of the invention.

The presently disclosed ophthalmic surgical instrument provides several advantages over the prior art. The ophthalmic surgical instrument presents a helical corkscrew having a harp beveled tip. The helical corkscrew has one or two 360 degrees turn configurations depending on the need. The helical corkscrew is twisted such that the tip rotates inside of the substance of the lens/cataract and allows the eye surgeon to remove the fluid from the cataract at different depths. In some embodiments, the ophthalmic surgical instrument connects to a syringe having a viscoelastic substance. The viscoelastic substance is injected into the eye through the helical corkscrew to keep the eye from collapsing as ophthalmic surgical instrument is being used. Further, the viscoelastic substance allows the eye surgeon to go deeper into the eye to impale the swollen cataract in a controlled manner.

A person skilled in the art appreciates that the ophthalmic surgical instrument can come in a variety of shapes and sizes depending on the need and comfort of the user. Further, many changes in the design and placement of components may take place without deviating from the scope of the presently disclosed ophthalmic surgical instrument.

In the above description, numerous specific details are set forth such as examples of some embodiments, specific components, devices, methods, in order to provide a thorough understanding of embodiments of the present invention. It will be apparent to a person of ordinary skill in the art that these specific details need not be employed, and should not be construed to limit the scope of the invention.

In the development of any actual implementation, numerous implementation-specific decisions must be made to achieve the developer's specific goals, such as compliance with system-related and business-related constraints. Such a development effort might be complex and time-consuming, but may nevertheless be a routine undertaking of design, fabrication, and manufacture for those of ordinary skill. Hence as various changes could be made in the above constructions without departing from the scope of the invention, it is intended that all matter contained in the above description or shown in the accompanying drawings shall be interpreted as illustrative and not in a limiting sense.

The foregoing description of embodiments is provided to enable any person skilled in the art to make and use the invention. Various modifications to these embodiments will be readily apparent to those skilled in the art, and the novel principles and invention disclosed herein may be applied to other embodiments without the use of the innovative faculty. It is contemplated that additional embodiments are within the spirit and true scope of the disclosed invention.

What is claimed is:

1. An ophthalmic surgical instrument, comprising:

a housing;

a wire connecting said housing; and a helical corkscrew extending from said wire, wherein said helical corkscrew has a 360 degree turn configuration, and wherein said helical corkscrew comprising an interior passage and a tip, wherein said tip is configured to impale a cataract by creating an opening in the cataract, wherein said helical corkscrew is configured to be twisted such that said tip rotates inside of the cataract allowing removal of the fluid at different depths, and pushes up pieces of the cataract for removal; and wherein said housing comprises a syringe body storing a viscoelastic substance, and wherein said syringe body is configured to inject the viscoelastic substance into the eye through said helical corkscrew to keep the eye from collapsing during use of the ophthalmic surgical instrument.

2. The ophthalmic surgical instrument of claim 1, wherein said syringe body is configured to operate to release the viscoelastic substance controllably allowing an eye surgeon to go deeper into the eye to impale the cataract in a controlled manner.

3. The ophthalmic surgical instrument of claim 2, wherein said syringe body comprises a plunger configured to provide negative pressure to decrease intralenticular pressure once the cataract is impaled.

4. The ophthalmic surgical instrument of claim 1, wherein said tip has a beveled edge.

5. The ophthalmic surgical instrument of claim 1, wherein said tip is angled.

6. An ophthalmic surgical instrument, comprising:

a housing;

a wire connecting said housing;

a helical corkscrew extending from said wire, wherein said helical corkscrew has a 360 degree turn configuration, and wherein said helical corkscrew comprising an interior passage and a tip, wherein said tip is angled;

an ultrasound handpiece connected to said housing, wherein said ultrasound handpiece is configured to transmit ultrasound waves to break up a cataract, wherein said tip is configured to impale the cataract by creating an opening in the cataract, and wherein said helical corkscrew is configured to be twisted such that said tip rotates inside of the cataract allowing removal of the fluid at different depths, and pushes up pieces of the cataract for removal; and wherein said housing comprises a syringe body storing a viscoelastic substance, and wherein said syringe body is configured to inject the viscoelastic substance into the eye through said helical corkscrew to keep the eye from collapsing during use of the ophthalmic surgical instrument.

7. The ophthalmic surgical instrument of claim 6, wherein said syringe body is configured to operate to release the viscoelastic substance controllably allowing an eye surgeon to go deeper into the eye to impale the cataract in a controlled manner.

8. The ophthalmic surgical instrument of claim 7, wherein said syringe body comprises a plunger configured to provide negative pressure to decrease intralenticular pressure once the cataract is impaled.

* * * * *